(12) United States Patent
Connors, III et al.

(10) Patent No.: US 11,000,670 B2
(45) Date of Patent: May 11, 2021

(54) FLEXIBLE SHEATH WITH VARYING DUROMETER

(75) Inventors: John J. Connors, III, Coral Gables, FL (US); Christopher G. Dixon, Bloomington, IN (US); Ray Leonard, II, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1110 days.

(21) Appl. No.: 10/831,813

(22) Filed: Apr. 26, 2004

(65) Prior Publication Data
US 2005/0090802 A1    Apr. 28, 2005

Related U.S. Application Data

(60) Provisional application No. 60/466,384, filed on Apr. 28, 2003.

(51) Int. Cl.
*A61M 25/00* (2006.01)
*A61M 25/06* (2006.01)

(52) U.S. Cl.
CPC ...... *A61M 25/0017* (2013.01); *A61M 25/005* (2013.01); *A61M 25/0054* (2013.01); *A61M 25/0662* (2013.01); *A61M 25/0053* (2013.01)

(58) Field of Classification Search
CPC ............ A61M 25/0017; A61M 25/005; A61M 25/0054; A61M 25/0662; A61M 25/0053
USPC .............................. 604/103.09, 526; 606/191
See application file for complete search history.

(56) References Cited

U.S. PATENT DOCUMENTS

| | | |
|---|---|---|
| 2,437,542 A | 3/1948 | Krippendorf |
| 2,857,915 A | 10/1958 | Sheridan |
| 3,174,851 A | 3/1965 | Buehler et al. |
| 3,228,894 A | 1/1966 | Jeckel |
| 3,351,463 A | 11/1967 | Rozner et al. |
| 3,370,587 A | 2/1968 | Vizcarra |
| 3,416,531 A | 12/1968 | Edwards |
| 3,485,234 A | 12/1969 | Stevens |
| 3,568,660 A | 3/1971 | Crites et al. |
| 3,608,555 A | 9/1971 | Greyson |
| 3,612,038 A | 10/1971 | Halligan |
| 3,618,614 A | 11/1971 | Flynn |
| 3,746,003 A | 7/1973 | Blake et al. |
| 3,749,134 A | 7/1973 | Slingluff et al. |
| 3,753,700 A | 8/1973 | Harrison |
| 3,866,599 A | 2/1975 | Johnson |

(Continued)

FOREIGN PATENT DOCUMENTS

WO    WO 01/07231 A1    2/2001

*Primary Examiner* — Amy R Weisberg
(74) *Attorney, Agent, or Firm* — Brinks Gilson & Lione (57) ABSTRACT

A flexible kink-resistant introducer sheath (10). The introducer sheath includes an inner liner (31), a coil (33) and an outer tube (33). The inner liner includes a passageway (30) extending longitudinally therethrough, where a catheter (50) can be advanced through the passageway. The coil (33) has a plurality of turns positioned longitudinally and compression fitted around the inner liner (31), where the turns have a predetermined spacing therebetween. The outer tube (20) is positioned longitudinally around the coil (33) and the inner liner (31), and is connected to the inner liner through the spaces between the turns. A diameter difference between the inner liner and the catheter is in a range of about 0.0005 to about 0.004 inch (0.013 to about 0.10 mm).

25 Claims, 4 Drawing Sheets

(56) References Cited

U.S. PATENT DOCUMENTS

| | | |
|---|---|---|
| 3,890,976 A | 6/1975 | Bazell et al. |
| 3,890,977 A | 6/1975 | Wilson |
| 3,924,632 A | 12/1975 | Cook |
| 3,935,857 A | 2/1976 | Co |
| 3,995,623 A | 12/1976 | Blake et al. |
| 4,015,601 A | 4/1977 | Bokros et al. |
| 4,024,873 A | 5/1977 | Antoshkiw et al. |
| 4,029,104 A | 6/1977 | Kerber |
| 4,099,425 A | 7/1978 | Moore |
| 4,117,836 A | 10/1978 | Erikson |
| 4,169,464 A | 10/1979 | Obrez |
| 4,184,497 A | 1/1980 | Kolff et al. |
| 4,196,731 A | 4/1980 | Laurin et al. |
| 4,248,234 A | 2/1981 | Assenza et al. |
| 4,265,276 A | 5/1981 | Hatada et al. |
| 4,276,874 A | 7/1981 | Wolvek et al. |
| 4,279,252 A | 7/1981 | Martin |
| 4,306,566 A | 12/1981 | Sinko |
| 4,329,993 A | 5/1982 | Lieber et al. |
| 4,345,602 A | 8/1982 | Yoshimura et al. |
| 4,361,152 A | 11/1982 | Patel |
| 4,362,163 A | 12/1982 | Krick |
| 4,368,730 A | 1/1983 | Sharrock |
| 4,385,635 A | 5/1983 | Ruiz |
| 4,425,919 A | 1/1984 | Alston, Jr. et al. |
| 4,464,176 A | 8/1984 | Wijayarathna |
| 4,484,586 A | 11/1984 | McMickle et al. |
| 4,498,473 A | 2/1985 | Gereg |
| 4,504,268 A | 3/1985 | Herlitze |
| 4,516,972 A | 5/1985 | Samson |
| 4,531,943 A | 7/1985 | Van Tassel et al. |
| 4,547,193 A | 10/1985 | Rydell |
| 4,551,292 A | 11/1985 | Fletcher et al. |
| 4,563,181 A | 1/1986 | Wijayarathna et al. |
| 4,571,240 A | 2/1986 | Samson et al. |
| 4,577,543 A | 3/1986 | Wilson |
| 4,596,563 A | 6/1986 | Pande |
| 4,610,674 A | 9/1986 | Suzuki et al. |
| 4,627,844 A | 12/1986 | Schmitt |
| 4,636,346 A | 1/1987 | Gold et al. |
| 4,639,246 A | 1/1987 | Dudley |
| 4,694,838 A | 9/1987 | Wijayarthna et al. |
| 4,696,304 A | 9/1987 | Chin |
| 4,705,511 A | 11/1987 | Kocak |
| 4,721,115 A | 1/1988 | Owens |
| 4,737,153 A | 4/1988 | Shimamura et al. |
| 4,739,768 A | 4/1988 | Engelson |
| 4,747,840 A | 5/1988 | Ladika et al. |
| 4,758,221 A | 7/1988 | Jureidini |
| 4,762,130 A | 8/1988 | Fogarty et al. |
| 4,775,371 A | 10/1988 | Mueller, Jr. |
| 4,806,182 A | 2/1989 | Rydell et al. |
| 4,817,613 A | 4/1989 | Jaraciewski et al. |
| 4,832,681 A | 5/1989 | Lenck |
| 4,840,622 A | 6/1989 | Hardy |
| 4,842,590 A | 6/1989 | Tanabe et al. |
| 4,863,442 A | 9/1989 | DeMello et al. |
| 4,883,058 A | 11/1989 | Ruiz |
| 4,884,579 A | 12/1989 | Engelson |
| 4,886,506 A | 12/1989 | Lovgren et al. |
| 4,898,591 A | 2/1990 | Jang et al. |
| 4,899,787 A | 2/1990 | Ouchi et al. |
| 4,960,410 A * | 10/1990 | Pinchuk .................... 604/96.01 |
| 4,963,306 A | 10/1990 | Weldon |
| 4,985,022 A | 1/1991 | Fearnot et al. |
| 4,994,069 A | 2/1991 | Ritchart et al. |
| 5,019,057 A | 5/1991 | Truckai |
| 5,037,404 A | 8/1991 | Gold et al. |
| 5,057,083 A | 10/1991 | Gellman |
| 5,057,092 A | 10/1991 | Webster, Jr. |
| 5,069,673 A | 12/1991 | Shwab |
| 5,069,674 A | 12/1991 | Fearnot et al. |
| 5,078,702 A | 1/1992 | Pomeranz |
| 5,085,649 A | 2/1992 | Flynn |
| 5,088,991 A | 2/1992 | Weldon |
| 5,116,652 A | 5/1992 | Alzner |
| 5,156,785 A | 10/1992 | Zdrahala |
| 5,160,559 A | 11/1992 | Scovil et al. |
| 5,163,431 A | 11/1992 | Griep |
| 5,171,232 A | 12/1992 | Castillo et al. |
| 5,176,660 A | 1/1993 | Truckai |
| 5,178,158 A | 1/1993 | de Toledo |
| 5,180,376 A | 1/1993 | Fischell |
| 5,217,482 A | 6/1993 | Keith |
| 5,221,255 A | 6/1993 | Mahurkar et al. |
| 5,221,270 A | 6/1993 | Parker |
| 5,226,911 A | 7/1993 | Chee et al. |
| 5,234,416 A | 8/1993 | Macaulay et al. |
| 5,248,305 A | 9/1993 | Zdrahala |
| 5,250,071 A | 10/1993 | Palermo |
| 5,254,107 A | 10/1993 | Soltesz |
| 5,261,916 A | 11/1993 | Engelson |
| 5,279,596 A | 1/1994 | Castaneda et al. |
| 5,286,259 A | 2/1994 | Ganguly et al. |
| 5,290,230 A | 3/1994 | Ainsworth et al. |
| 5,294,325 A | 3/1994 | Liu |
| 5,304,194 A | 4/1994 | Chee et al. |
| 5,304,195 A | 4/1994 | Twyford, Jr. et al. |
| 5,306,252 A | 4/1994 | Yutori et al. |
| 5,306,262 A | 4/1994 | Weldon |
| 5,308,342 A | 5/1994 | Sepetka et al. |
| 5,312,415 A | 5/1994 | Palermo |
| 5,314,418 A | 5/1994 | Takano et al. |
| 5,334,169 A | 8/1994 | Brown et al. |
| 5,334,171 A | 8/1994 | Kaldany |
| 5,336,205 A | 8/1994 | Zenzen et al. |
| 5,342,295 A | 8/1994 | Imran |
| 5,342,383 A | 8/1994 | Thomas |
| 5,342,386 A | 8/1994 | Trotta |
| 5,348,536 A | 9/1994 | Young et al. |
| 5,356,388 A | 10/1994 | Sepetka et al. |
| 5,380,304 A | 1/1995 | Parker |
| 5,397,306 A | 3/1995 | Nobuyoshi et al. |
| 5,403,292 A | 4/1995 | Ju |
| 5,423,773 A | 6/1995 | Jimenez |
| 5,472,435 A | 12/1995 | Sutton |
| 5,484,565 A | 1/1996 | Larsen et al. |
| 5,489,269 A | 2/1996 | Aldrich et al. |
| 5,496,294 A | 3/1996 | Hergenrother et al. |
| 5,514,236 A | 5/1996 | Avellanet et al. |
| 5,531,721 A | 7/1996 | Pepin et al. |
| 5,545,149 A | 8/1996 | Brin et al. |
| 5,569,218 A | 10/1996 | Berg |
| 5,599,325 A | 2/1997 | Ju et al. |
| 5,599,326 A | 2/1997 | Carter |
| 5,601,538 A | 2/1997 | Deem |
| 5,603,705 A | 2/1997 | Berg |
| 5,658,263 A | 8/1997 | Dang et al. |
| 5,674,208 A | 10/1997 | Berg et al. |
| 5,676,659 A | 10/1997 | McGurk |
| 5,700,253 A | 12/1997 | Parker |
| 5,702,373 A | 12/1997 | Samson |
| 5,725,513 A | 3/1998 | Ju et al. |
| 5,755,704 A | 5/1998 | Lunn |
| 5,769,830 A | 6/1998 | Parker |
| 5,772,641 A | 6/1998 | Wilson |
| 5,791,036 A | 8/1998 | Goodin et al. |
| 5,792,124 A | 8/1998 | Horrigan et al. |
| 5,807,350 A | 9/1998 | Diaz |
| 5,811,043 A | 9/1998 | Horrigan et al. |
| 5,836,925 A | 11/1998 | Soltesz |
| 5,851,203 A | 12/1998 | van Muiden |
| 5,860,963 A | 1/1999 | Azam et al. |
| 5,897,537 A | 4/1999 | Berg et al. |
| 5,906,605 A | 5/1999 | Coxum |
| 5,911,715 A | 6/1999 | Berg et al. |
| 5,938,653 A | 8/1999 | Pepin |
| 5,947,939 A | 9/1999 | Mortier et al. |
| 5,951,495 A | 9/1999 | Berg et al. |
| 5,951,539 A * | 9/1999 | Nita et al. ...................... 604/526 |
| 5,951,929 A | 9/1999 | Wilson |
| 5,954,651 A | 9/1999 | Berg et al. |
| 5,964,971 A | 10/1999 | Lunn |
| 5,971,975 A | 10/1999 | Mills et al. |

(56) References Cited

U.S. PATENT DOCUMENTS

| | | |
|---|---|---|
| 5,972,441 A | 10/1999 | Campbell et al. |
| 5,976,120 A | 11/1999 | Chow et al. |
| 5,980,505 A | 11/1999 | Wilson |
| 6,025,044 A | 2/2000 | Campbell et al. |
| 6,027,779 A | 2/2000 | Campbell et al. |
| 6,040,547 A | 4/2000 | Ren et al. |
| 6,059,769 A | 5/2000 | Lunn et al. |
| 6,077,258 A | 6/2000 | Lange et al. |
| 6,090,099 A | 7/2000 | Samson et al. |
| 6,103,037 A | 8/2000 | Wilson |
| 6,106,540 A | 8/2000 | White et al. |
| 6,152,912 A | 11/2000 | Jansen et al. |
| 6,165,165 A | 12/2000 | Cecchi et al. |
| 6,168,588 B1 | 1/2001 | Wilson |
| 6,171,296 B1 * | 1/2001 | Chow .......................... 604/525 |
| 6,186,986 B1 | 2/2001 | Berg et al. |
| 6,193,705 B1 | 2/2001 | Mortier et al. |
| 6,197,015 B1 | 3/2001 | Wilson |
| 6,217,565 B1 | 4/2001 | Cohen |
| 6,251,093 B1 * | 6/2001 | Valley et al. .............. 604/97.03 |
| 6,254,592 B1 | 7/2001 | Samson et al. |
| 6,296,631 B2 | 10/2001 | Chow |
| 6,328,731 B1 | 12/2001 | Ouchi |
| 6,355,027 B1 | 3/2002 | Le et al. |
| 6,368,316 B1 | 4/2002 | Jansen et al. |
| 6,398,791 B1 | 6/2002 | Que et al. |
| 6,451,005 B1 | 9/2002 | Saitou et al. |
| 6,503,353 B1 | 1/2003 | Peterson et al. |
| 6,508,804 B2 | 1/2003 | Sarge et al. |
| 6,508,805 B1 | 1/2003 | Garabedian et al. |
| 6,524,303 B1 | 2/2003 | Garibaldi |
| 6,533,751 B2 | 3/2003 | Cragg et al. |
| 6,652,508 B2 | 11/2003 | Griffin et al. |
| 6,706,025 B2 | 3/2004 | Engelson et al. |
| 2001/0034514 A1 | 10/2001 | Parker |
| 2002/0022831 A1 | 2/2002 | O'Connor et al. |
| 2002/0032408 A1 * | 3/2002 | Parker et al. ............ 604/103.09 |
| 2004/0153049 A1 * | 8/2004 | Hewitt .............. A61M 25/0012 604/527 |

* cited by examiner

FIG. 5

FLEXIBLE SHEATH WITH VARYING DUROMETER

RELATED APPLICATION

The present patent document claims the benefit of the filing date under 35 U.S.C. § 119(e) of Provisional U.S. Patent Application Ser. No. 60/466,384, filed Apr. 28, 2003, which is hereby incorporated by reference.

BACKGROUND

Technical Field. This invention relates generally to medical devices and, in particular, to a delivery catheter or sheath and, more particularly, to a flexible, kink-resistant introducer sheath having a plurality of distal segments that are of decreasing durometer.

Background Information. Introducer catheters or sheaths are widely used to provide a conduit for percutaneous access to the vascular system. Such sheaths are generally of thin-wall construction, and thus, have a tendency to kink when traversing within the narrow confines of the vascular system. Increasing the thickness of the sheath wall minimally improves the level of kink resistance, however this level is still often considered unacceptable. In addition, increasing the thickness of the sheath wall is generally considered undesirable, because it necessitates the use of a larger entry hole than would otherwise be required.

Sheaths used in certain medical procedures wherein a fluid is to be introduced and/or removed from the vasculature of a patient, such as hemofiltration and dialysis, are particularly prone to kinking, since such sheaths remain positioned in a patient's body for an extended period of time. While positioned in a patient, the sheath may be bent or pinched off and, as a result, kink due to repeated use or patient movement. A kinked sheath is unusable and cannot be straightened while positioned in the body of a patient. Consequently, the sheath must be removed, leaving an enlarged, bleeding opening which typically cannot be reused. Vascular access must then be re-attempted at an alternative site, and the procedure is restarted. Restarting the procedure causes a time delay, which is inconvenient, and at times may be life threatening. In addition, in some cases, an acceptable alternative site is not available for introducing another sheath.

Another problem with existing introducer sheaths is that the sheath may kink when a physician attempts to insert an interventional device, such as a catheter or a stent, through the sheath during an emergency procedure. Small diameter introducer sheaths are particularly prone to being bent and kinked under the time constraints that arise during an emergency situation. If kinking occurs, the sheath becomes unusable and a new sheath must be introduced at the same or another access site.

Introducer sheaths are widely used for delivering an implantable medical device, such as a stent or a stent graft, to a deployment site well within the vasculature of the patient. However, catheters or sheaths used to deliver such devices are susceptible to kinking, particularly when the implantable medical device or pusher does not have a uniform diameter to reinforce the delivery catheter or sheath along its entire length. The possibility of kinking is increased when the sheath is to be used to introduce an implantable device into one of the many smaller vessels that branch off from major vessels, such as the aorta. In this event, the sheath may not have enough flexibility at the very point where such flexibility is required in order to enable proper positioning of the device.

It is desired to provide an introducer sheath that has sufficient stiffness to permit it to be introduced into the vascular system to perform an interventional procedure, and yet is sufficiently flexible at designated areas of the sheath to permit it to be directed to one or more small branch vessels.

BRIEF SUMMARY

The present invention has been accomplished in view of the above-mentioned technical background, and it is an object of the present invention to provide a sheath that allows a user to readily traverse vessels in a patient's vasculature to contact small tortuous vessels and deliver or remove materials without causing undue damage to any part of the patient's body.

In one embodiment, the invention comprises a flexible, kink-resistant introducer sheath. The introducer sheath includes an inner tube having a passageway extending longitudinally therethrough, a coil comprising a plurality of turns positioned longitudinally around the inner tube, and an outer tube positioned longitudinally around the coil and inner tube and connected to the inner tube through spaces between the coil turns. The outer tube comprises a plurality of tube segments aligned in order of decreasing durometer from the proximal end of the sheath to the distal end.

In another embodiment, the invention comprises a sheath and catheter assembly. The assembly comprises a sheath having an inner tube having a passageway extending longitudinally therethrough, a coil comprising a plurality of turns positioned longitudinally around the inner tube, and an outer tube positioned longitudinally around the coil and connected to the inner tube through the spaces between the turns. The outer tube comprises a plurality of tube segments aligned in order of decreasing durometer toward the distal end of the sheath. The catheter is sized for insertion into the inner passageway of the tube, and is further sized such that at least a portion of the distal end of the catheter extends beyond the distal end of the sheath when the catheter is inserted into the passageway. The catheter has an outer diameter that is 0.0005 to 0.004 inch (0.013 to 0.10 mm) less than the diameter of the passageway.

In yet another embodiment, the invention comprises a method for inserting an introducer sheath into a patient's vasculature. In the inventive method, a wire guide is inserted into the patient's vasculature. A dilator is threaded over the wire guide into the vasculature, the dilator being positioned within the passageway of an introducer sheath. The sheath comprises an inner tube, a coil comprising a plurality of turns positioned longitudinally around the inner tube, and an outer tube positioned longitudinally around the coil and inner tube. The outer tube comprises a plurality of tube segments aligned in order of decreasing durometer from the proximal end to the distal end of the sheath. The dilator is withdrawn from the sheath, while leaving the sheath in the vasculature. A catheter having a distal end shaped to facilitate entry into remote areas of the vasculature is inserted into the vasculature through the sheath passageway, and a remote area is thereafter accessed via the shaped distal end.

DETAILED DESCRIPTION OF THE DRAWINGS AND THE PRESENTLY PREFERRED EMBODIMENTS

Figure 1:
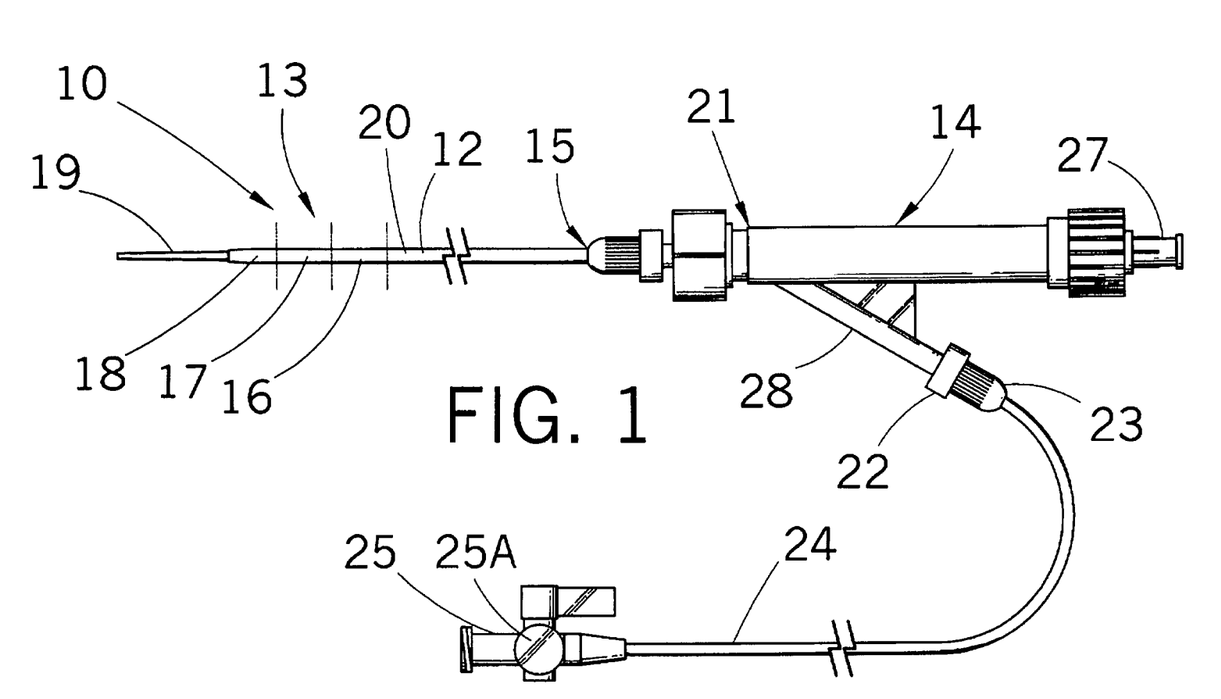
FIG. 1 depicts an illustrative sheath of the present invention, shown in combination with a dilator and a manifold.

FIG. 1 depicts an illustrative flexible, kink-resistant, introducer sheath 10, according to an embodiment of the present invention. Sheath 10 is shown in combination with a dilator 11 and a connector valve 14.

In the embodiment shown, sheath 10 includes an outer tube 20, which is provided with a proximal end 15 and a distal end 13. Proximal end 15 may be formed into either a straight or a flared configuration in conventional fashion. Distal end 13 may be tapered, and may have a straight shape, a curved shape, a J-shape or any other shape that will facilitate the entry of the distal end 13 into a vascular anatomy. Outer tube 20 comprises a plurality of discrete segments 12, 16, 17, 18 of different durometer.

In the embodiment of FIG. 1, connector valve 14 comprises a well-known Tuohy-Borst Side-Arm Adapter. The Tuohy-Borst Adapter includes a valve seal (not shown) for minimizing blood loss during insertion of the sheath. Adapters of this type are available from Cook Incorporated, of Bloomington, Ind. Connector valve 14 allows a user to inject fluid through the sheath 10 into the vascular anatomy. The connector valve shown includes a "Y"-connector 21. Arm 28 of Y-connector 21 is coupled to a suitable second connector 22, which is coupled to a third connector 23. A suitable polymeric tube, such as polyvinyl tube 24, extends from connector 23 to a high-flow three-way stopcock connector 25, for use in introducing and aspirating fluids therethrough. The high-flow three-way stopcock connector 25 includes a plug 25a for selectively allowing and preventing fluids from flowing through the stopcock connector. Those skilled in the art will appreciate that connector valve 14 need not be of the exact configuration shown, and that any manifold of the type commonly used in the art for such purposes may be substituted for connector valve shown. If desired, such manifolds may be provided with additional side-arms to enhance the utility of the device, such as the introduction and/or aspiration of additional fluids.

Figure 2:
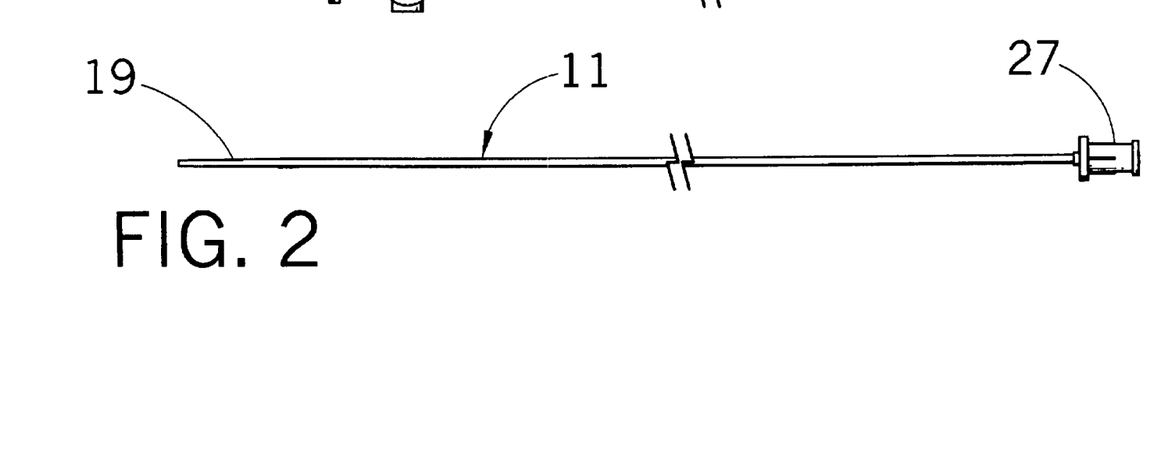
FIG. 2 depicts the dilator of FIG. 1 removed from the sheath.

As shown in FIG. 2, dilator 11 has a proximal end 27 and a distal end 19. Distal end 19 is tapered for accessing and dilating a vascular access site. Dilator 11 includes a lumen therethrough for passage of a wire guide using, for example, the well-known Seldinger technique. Dilator 11 is sized such that when its proximal end 27 abuts against the proximal end of connector valve 14, approximately 10-15 cm of dilator distal end 19 protrudes from the distal end of sheath 10. Preferably, the dilator has an outside diameter of about 4-8 French. A preferred dilator is a Coons dilator, available from Cook Incorporated, of Bloomington, Ind.

Figures 3, 4:
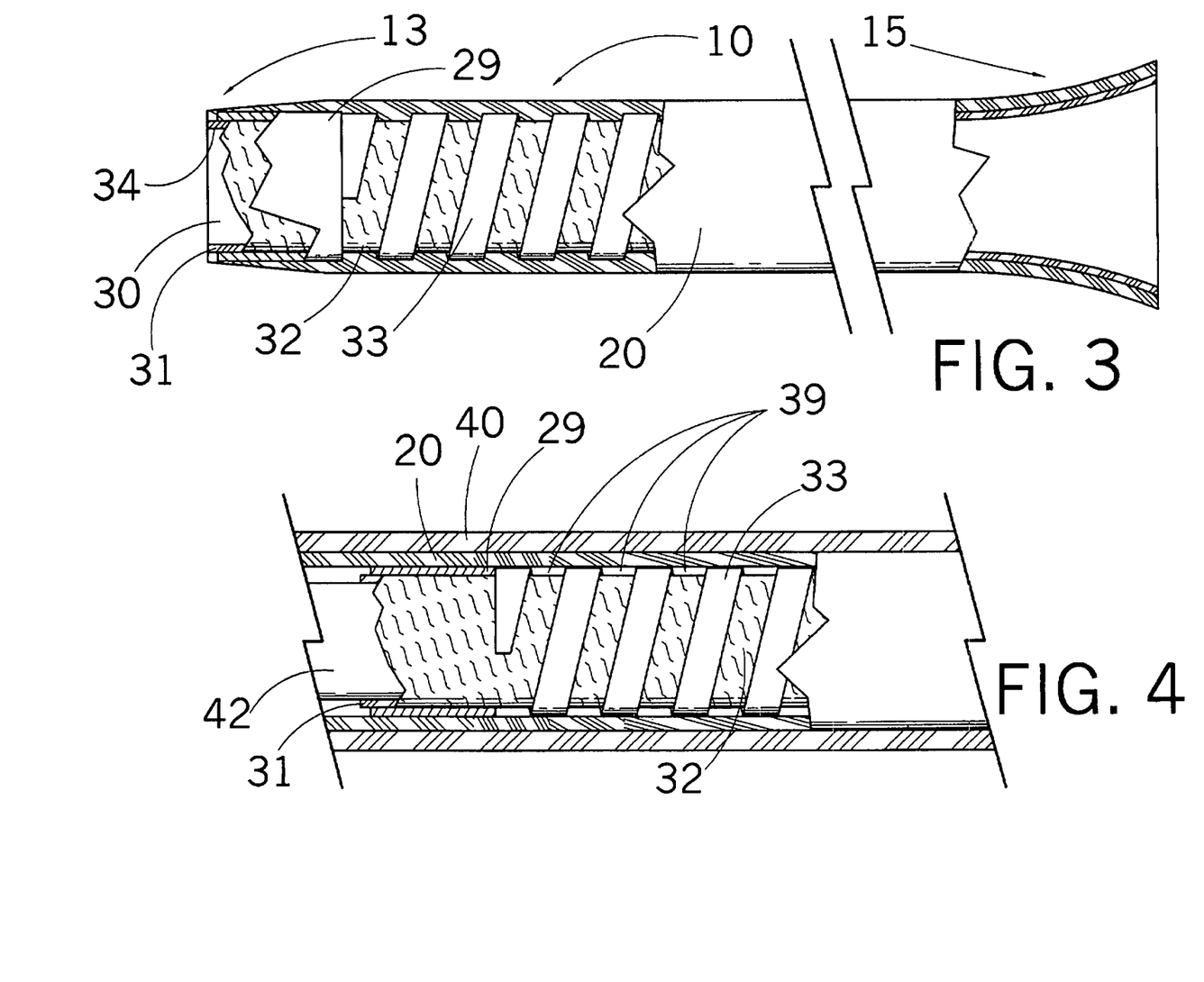
FIG. 3 depicts a partially sectioned view of sheath of FIG. 1, with the dilator removed.
FIG. 4 depicts a partially sectioned view of the inventive sheath enveloped by a heat shrink tube, prior to heating of the sheath.

FIG. 3 depicts an enlarged, partially sectioned view of introducer sheath 10 of FIG. 1, with dilator 11 and connector valve 14 removed for clarity. Sheath 10 comprises an inner tube 31, a flat wire coil 33 wound or compression fitted around inner tube 31, and an outer tube 20. Preferably, outer tube 20 is mechanically connected to a roughened outer surface 32 of the inner tube 31 through the spacings of the coil 33. Outer surface 32 of the inner tube 31 may be chemically etched in well-known manner for forming the roughened outer surface.

In a preferred embodiment, inner tube 31 comprises a lubricious material, preferably a fluorocarbon such as polytetrafluoroethylene (PTFE). Preferably, inner tube 31 has a uniform inside diameter having an inside diameter ranging from about 4 to 10 French, more preferably, from 5 to 8 French. The wall thickness of inner tube 31 is generally about 0.0015 inch (0.038 mm). These dimensions are exemplary only, and the inner diameter may be constructed to be of any size necessary to accomplish the purposes for which the sheath is to be employed. The lubricious PTFE material presents a slippery inner surface 34 to allow easy insertion and withdrawal of the dilator 11 as well as other catheters and medical apparatus. Inner surface 34 is also smooth and nonporous for minimizing the formation of blood clots and other thrombi thereon.

The uniform inner diameter of inner tube 31 extends the entire length of passageway 30 to enable passage of the largest possible diameter catheter or other interventional device therethrough. The wall of the inner tube 31 has sufficient radial rigidity to prevent the turns of compression-fitted coil 33 from protruding into inner tube passageway 30.

Coil 33 may be compression fitted or wound around inner tube 31. The coil includes a plurality of turns, and preferably includes uniform spacings between the coil turns. Preferably coil 33 is stainless steel flat wire, although other biologically compatible metals, alloys (including super-elastic alloys), and composite materials may also be utilized. In addition, although a flat wire coil is preferred, coils of other cross-sectional dimensions, such as round wire, may also be utilized. When flat wire stainless steel is used, coil 33 is preferably formed from wire that is about 0.003 inch thick by 0.012 inch wide (0.076 mm by 0.30 mm). Preferably, the ends of coil 33 are spaced approximately 5 mm from the distal end of inner tube 31 and approximately 1.4 cm from the proximal end. This spacing permits tapering of the distal tube end and flaring of the proximal end. Preferably, the turns of coil 33 are uniformly spaced apart by approximately 0.3 mm. Although it is preferred to use coils having uniformly spaced turns and a constant pitch, this is not required and coils spaced non-uniform distances, or at a varying coil turn pitch may also be used.

Sheath 10 may be constructed to have any length required to fulfill its intended purposes. In most cases, the sheath will have a length between about 50 and 125 cm, and most generally, between about 70 and 100 cm. Generally, the lengths of inner tube 31 and outer tube 20 are the same, and the length of coil 33 will be less than the length of the inner and outer tubes, for the purposes recited in the previous paragraph. For an exemplary sheath of 70-90 cm length, the distal portion, for example the distal 60 cm, cm may be covered with a hydrophilic coating, such as AQ® hydrophilic coating.

Outer tube 20 is formed of any well-known polymer commonly used for such purpose. Preferably, outer tube 20 comprises a heat formable polyamide material, such as nylon. This heat formable material melts upon heating, such that portions flow between the turns of the coil and bond to the roughened outer surface of the inner tube. The pre-melt thickness of the wall of the nylon tube is approximately 0.0065 inch (0.17 mm) for exemplary sheaths of 5-8 French.

In order to construct the sheath 10 according to a preferred embodiment of the present invention, inner tube 31 is positioned over a stainless steel mandril 42 as shown in FIG. 4, such that the inner diameter (ID) of the inner tube 31 substantially matches the outer diameter (OD) of the mandril. A flat wire coil 33 having an ID less than the OD of inner tube 31 is compression fitted or wound around the inner tube. Suitable techniques for compression fitting and winding coils are well known in the art.

A long, or "major" segment 12, such as a segment having a length of e.g. 50-100 cm, or even more preferably 55-85 cm, of the outer tube 20 is longitudinally positioned around inner tube 31 and flat wire coil 33. Preferably, major segment 12 has a durometer in the range of about 70 to 80 on the Shore D scale, most preferably about 75. The term "durometer" as used herein is a common term of art that is normally used to refer to the resistance of materials such as rubber or plastics to deformation, typically to deformation by an indenter of specific size and shape under a load. The Shore D scale is a common measure of hardness of plastic materials. A high durometer material is one that is relatively inflexible (e.g. harder), whereas a low durometer material is one that is relatively flexible (e.g. softer). All durometer readings herein are measured on the Shore D scale.

A plurality of smaller, or "minor", tube segments 16, 17, 18 of decreasing durometer, to be described in greater detail, extend from major segment 12 to the distal end of the sheath. Preferably, the length of the major segment comprises at least 50% of the length of the outer tube, more preferably at least 75%, and even more preferably at least 80-85%. In one preferred embodiment, none of the three minor segments 16, 17, 18 exceeds about 5 cm in length.

Following positioning of major segment 12 as described, segment 16 is then positioned such that it abuts the distal end of segment 12. In a preferred embodiment, segment 16 has a length of about 3 cm, and a durometer in the range of about 53-63, preferably 58. Segment 17 is positioned to abut the distal end of segment 16. Segment 17 has a length of about 5 cm, and a durometer of about 35 to 45, preferably 40. Finally, in this embodiment, segment 18 is positioned to abut the distal end of segment 17. Segment 18 has a length of about 3.2 cm, and a durometer of about 20 to 30, preferably 25. Preferably, segments 16, 17 and 18 are also longitudinally positioned around the inner tube 31 and flat wire coil 33, in the same manner as segment 12, although if desired, coil 33 may be sized to terminate prior to one or more of the distal-most segments. If desired, a radiopaque marker band 29 may be slid under distal segment 18. Marker bands are well known in the art, and a band formed of any conventional materials may be utilized. Preferably, marker band 29 is formed of platinum.

The reduction in durometer of segments 12, 16, 17, 18 provides a gradual step-down at the distal end of sheath 10 from a relatively stiff shaft portion 12 to a relatively soft distal tip portion 18 without abrupt transitions. The stiff shaft portion 12 provides the shaft with trackability and non-kinking support over a rather long portion of the sheath, and the flexible distal tip enables the tip to be as benign as possible. An abrupt transition may otherwise prevent tracking of the sheath into remote areas of the vasculature, e.g., the common carotid from the aorta. In one preferred embodiment, the durometer of the major segment is between about 70 and 80 on the Shore D scale, and the durometers of the minor segments range between about 20 and 65 on the Shore D scale.

After outer tube segments 12, 16, 17, 18 have been positioned on inner tube 31 and flat wire coil 33 as described, heat shrink tube 40 is positioned such that it envelopes inner tube 31, flat wire coil 33, and outer tube segments 12, 16, 17, 18, as shown in FIG. 4. Heat shrink tube 40 is somewhat longer than outer tube 20, and is preferably formed of a fluorinated ethylene propylene heat shrinkable material.

Figure 5:
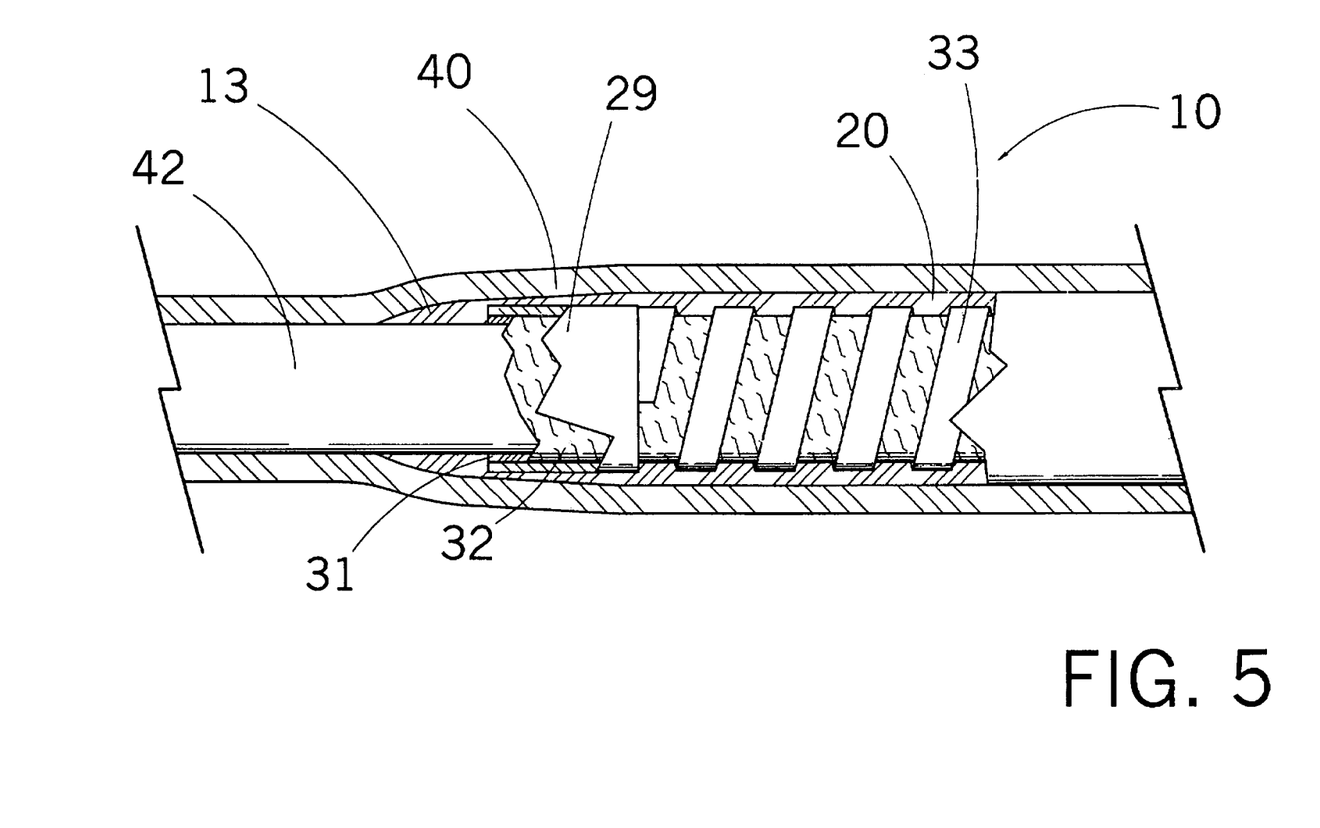
FIG. 5 depicts a partially sectioned view of the sheath of FIG. 4 after the sheath outer layer has been melted and prior to removal of the heat shrink tube.

Prior to heating, a space 39 exists between outer tube 20 and inner tube 31, as well as between the turns of the coil. When exposed to elevated temperatures in an oven, heat shrinkable tubing 40 shrinks and causes outer tube segments 12, 16, 17, 18 to melt. The melted segments flow between the uniform spacings of the turns of coil 33 and mechanically connect to roughened outer surface 32 of inner tube 31, as shown in FIG. 5. The shrink tube is then cut off, and the mandril is removed.

The heat formable nylon tube is self-leveling, which provides a uniform outer diameter surface for outer tube 20. Distal end 13 may be tapered to provide a smooth transition to inner dilator 11 or to a catheter. As a consequence of the heat treatment, the respective longitudinal ends of the four segments 12, 16, 17, 18 of different durometer nylon tubing bond/melt together to form a single sheath with three transitions, namely the transition between segments 12 and 16, the transition between segments 16 and 17, and the transition between segments 17 and 18. The varying durometers of the segments of outer tube 20 transition the sheath from a rigid shaft at outer tube segment 12 to a soft tip at segment 18. Other details of the construction of sheath 10 are conventional and need not be repeated here. Such details are discussed, among others, in U.S. Pat. No. 5,380,304, incorporated by reference herein.

Following is a description of an example of the use of sheath 10 in performing an interventional procedure. In this example, sheath 10 is used for placing an interventional device, such as a stent, into a patient's carotid artery. To initiate the procedure, a needle puncture is made through the patient's skin into a target vessel. A wire guide is then inserted through a bore in the needle into the vessel in accordance with the Seldinger technique, and the needle is withdrawn. A dilator and sheath combination as shown in FIG. 1 is then threaded over the wire guide. The dilator dilates the opening and provides a path to the desired area of the vasculature, in this case the aortic arch. In an alternate design, a dilator may be inserted followed by introduction of the sheath. In either case, once the distal end of the dilator reaches the aortic arch, the dilator is withdrawn from the sheath.

Figure 6:
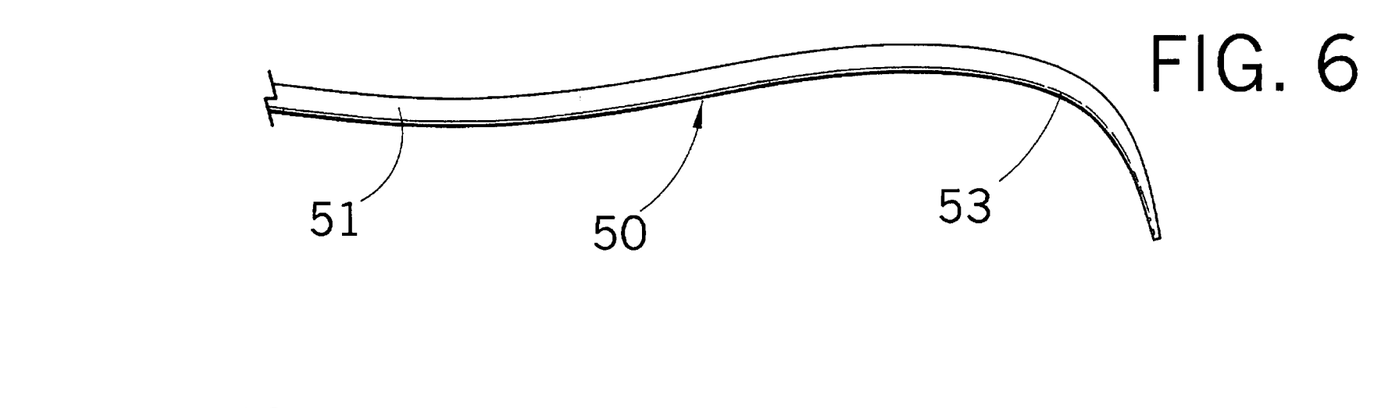
FIG. 6 depicts a catheter that may be used with the inventive sheath.
Figure 7:
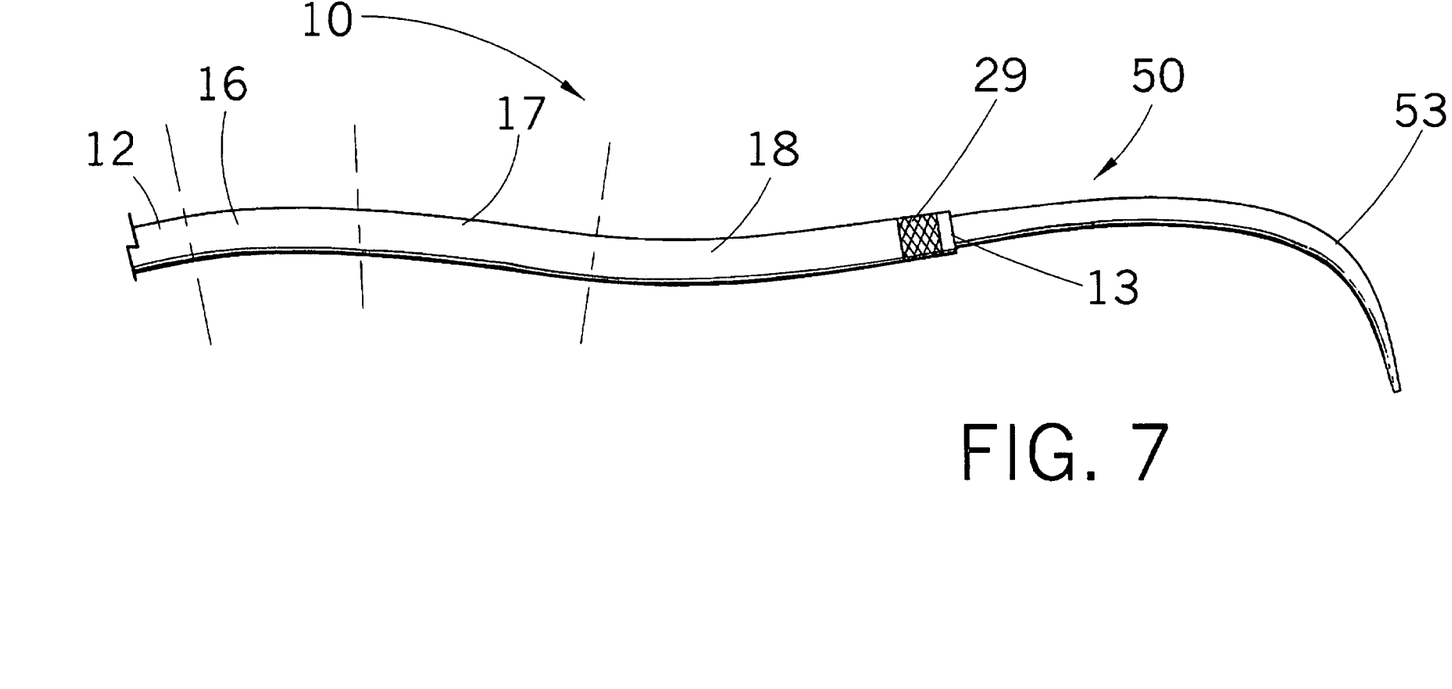
FIG. 7 depicts the catheter and sheath in combination.

A catheter 50 is then inserted over the wire guide into the sheath through the area vacated by the dilator. FIG. 6 illustrates one example of a catheter that may be used to access a smaller branch vessel in the patient's vasculature. Catheter 50 has a proximal end 51 and a distal end 53. If desired, distal end 53 may be formed of a radiopaque material. Preferably, catheter 50 comprises a nylon construction having a stainless steel braid within the nylon to provide enhanced torque. Distal end 53 of catheter 50 may include a curve or angle of a pre-selected configuration, to enable distal end 53 to mimic the vascular pattern at the target site to the extent feasible, and thereby facilitate insertion of the catheter and wire guide into the selected smaller vessel site. Catheter 50 may be constructed or formed to have virtually any shape that may be desired for a particular purpose. FIG. 7 shows catheter 50 inserted into sheath 10. As shown, the distal end 53 of catheter 50 extends in the distal direction beyond the distal end 13 of sheath 10. Conventional marker band 29 may be provided at the distal end of sheath 10.

The smaller neurocirculation vessels that may be a target of the technician comprise a tortuous pathway that branches off from the aorta. The neurocirculation target vessels include arch vessels like the subclavian vessels, the left common carotid and the innominate/brachiocephalic arteries. The curved distal end 53 of catheter 50 can be manipulated to enter into the desired area. The sheath can then be telescoped over the catheter that previously protruded from the end of the sheath inside the desired remote vessel, and catheter 50 can be removed. An interventional procedure, such as the placement of a stent (with or without a balloon), may now be performed. The flexibility of the sheath at the distal tip enables it to be benign in, e.g., the common carotid as the beating heart causes it to bob up and down.

A particularly preferred catheter that may be used with the inventive sheath is a selected one of the family of catheters known as SLIP-CATH® catheters, manufactured by Cook Incorporated, of Bloomington, Ind. SLIP-CATH® catheters are provided in a variety of sizes and distal-end configurations, to enable the physician to select an optimally-shaped catheter for a particular application. SLIP-CATH® catheters are provided in configurations particularly suitable for cerebral or visceral use. The catheter shown in FIG. 6 includes merely one example of a distal tip configuration that may be utilized. Those skilled in the art will recognize that many other tip configurations may be utilized for a particular application. The catheters may be provided in any convenient length from about 40 to 150 cm. When utilized in combination with a sheath having a length of from about 70 to 100 cm, the optimal lengths of such catheters are about 120 to 140 cm, preferably 125 cm.

In addition to the foregoing, it is preferred that the catheter be sized such that its outer diameter is between about 0.0005 and 0.004 inch (0.013 and 0.10 mm), less than the inner diameter of the sheath 10. Thus, for example, if the inner diameter of the inner tube 31 is about 0.100 inch (2.54 mm), then the outer diameter of the catheter is in range of about 0.0995 inch (2.53 mm) to about 0.096 inch (2.44 mm). More preferably, the difference in inner diameter of the sheath 10 to the catheter is about 0.001 inch (0.025 mm) to about 0.003 inch (0.076 mm).

The close tolerance between the sheath and the catheter prevents the catheter from knocking loose any plaque that may be lining the inside of the vessels traversed by the sheath and the catheter. This is often referred to as the "snowplowing" effect. Having a diameter difference is this range is also advantageous because it provides a smooth transition between the catheter and the sheath as the catheter is advanced through the sheath to a vessel within the vasculature of the patient. If the diameter difference is much greater than about 0.004 inch (0.10 mm), a ledge-type surface may be created. Upon insertion of the catheter or sheath into the vasculature, the presence of such a ledge could damage the anatomy of any vessel that is traversed by the component as it is being advanced. On the other hand, if the difference is much less than about 0.0005 inch (0.013 mm), there would be virtually no difference, or perhaps even an interference fit, between the surfaces. This will hinder the relative axial movement between the catheter and the sheath, thereby causing difficulty during the insertion and/or removal of the catheter from the sheath.

It is preferred that at least the distal portion of the catheter include a hydrophilic coating, such as the AQ® hydrophilic coating. A hydrophilic coating greatly increases the lubricity of the catheter when compared to non-coated catheters, and provides for ease of insertion and/or removal of the catheter. Preferably, the hydrophilic coating will comprise about the distal 60 cm of the catheter. In addition, it is preferred to utilize a catheter having a radiopaque distal tip portion. This may be formed by loading the polymeric matrix of the catheter with a suitable radiopaque material, such as tungsten. Alternatively, a radiopaque marker band may be positioned around a distal portion of the catheter in conventional fashion.

It is not necessary to use a dilator 11 in all applications. In some applications, the combination of sheath and catheter 50 can be used to dilate the initial opening, and the step of using a separate dilator 11 may be omitted.

The durometer ranges recited above are preferred because they provide a sheath that has the versatility to be used for a wide variety of applications. However, those skilled in the art will recognize that other durometer ranges may be substituted, and indeed, may be preferred for any specific application. The scope of the invention includes any sheath having a gradual decrease in durometer at the distal end to permit manipulation of the sheath such that it can be introduced into small diameter tortuous passages in the vasculature. Preferably, it is only the extreme distal end of the sheath, such as the distal 25 to 30 cm, preferably 10 to 15 cm, that is varied in durometer from the main body 12 of the sheath, although additional variations are possible. Decreasing the durometer over a plurality of segments, such as the three segments 16, 17, 18 over the distal 11.2 cm of the exemplary sheath described, provides a gradual decrease in stiffness, such as the described durometer decrease from 75 to 25, in precisely the area of the sheath that is often most in need of such variation. However, those skilled in the art may prefer a sheath having a more gradual decrease in durometer over a greater, or lesser, length of the sheath, which variation is also within the scope of the invention.

Although the exemplary sheath described above includes four segments 12, 16, 17, 18, a sheath according to the present invention may have more, or less, than four segments. For example, the distal end need not be limited to three relatively short segments, and can include as many segments as desired, as long as the segments are aligned to provide a gradual decrease in stiffness (increase in flexibility). Given the numerous and varied pathways in the human or animal vasculature, a sheath can be constructed according to the teachings of the present invention to conform specifically to virtually any particular vascular configuration. The dimensions provided above are only exemplary, but are believed to provide a sheath having sufficient versatility to be useful in a multitude of applications.

It is therefore intended that the foregoing detailed description be regarded as illustrative rather than limiting, and that it be understood that it is the following claims, including all equivalents, that are intended to define the spirit and scope of this invention.

The invention claimed is:

1. A flexible, kink-resistant introducer sheath, said sheath having a proximal end and a distal end, comprising:
   an inner tube having a passageway extending longitudinally therethrough, said passageway having a substantially uniform diameter;
   a coil comprising a plurality of turns positioned longitudinally around said inner tube, said turns having a predetermined spacing therebetween; and
   an outer tube positioned longitudinally around said coil and said inner tube and connected to said inner tube through the spaces between said turns, said outer tube having a diameter of greater than 5 French, and said outer tube comprising a plurality of tube segments aligned in order of decreasing durometer from said proximal end to said distal end, said plurality of segments comprising a major segment of higher durometer comprising at least 75% of the length of the outer tube, and three minor segments of lower durometer; and wherein the three minor segments are sized to access the common carotid, a most-distal minor segment of the three minor segments having a length of 3.2 cm and a durometer of between 20-30 on the Shore D Scale, a second-most-distal minor segment being the longest of the three minor segments, the second-most-distal minor segment having a length of 5 cm and a durometer of between 35-45 on the Shore D Scale, wherein the second-most-distal minor segment is immediately proximal from a most-distal minor segment of the three minor segments, and a third-most-distal minor segment of the three minor segments having a length of 3 cm and a durometer of between 53-63 on the Shore D Scale, wherein the third-most-distal minor segment is immediately proximal from the second-most-distal minor segment.

2. The introducer sheath of claim 1, wherein said substantially uniform diameter of said passageway ranges from 4 through 10 French.

3. The introducer sheath of claim 2, wherein the substantially uniform diameter is 6 or 7 French.

4. The introducer sheath of claim 1, wherein said inner tube comprises a lubricious material.

5. The introducer sheath of claim 4, wherein said inner tube comprises PTFE.

6. The introducer sheath of claim 5, wherein said PTFE tube has a roughened outer surface, and said outer tube is bonded to said inner tube at said roughened surface.

7. The introducer sheath of claim 1, wherein said turns are spaced apart a uniform distance.

8. The introducer sheath of claim 1, wherein said coil is spaced from at least one of the ends of the sheath.

9. The introducer sheath of claim 1, wherein said outer tube comprises a heat formable polyamide material.

10. The introducer sheath of claim 9, wherein said heat formable polyamide comprises nylon.

11. The introducer sheath of claim 1, wherein said sheath has a length of 70 to 100 cm, and wherein said sheath comprises three minor segments, wherein said minor segments in the aggregate comprise no greater than 11.2 cm of the length of the sheath.

12. The introducer sheath of claim 1, wherein the durometer of said major segment is between 70 and 80 on the Shore D scale.

13. The introducer sheath of claim 12, wherein the durometer of said major segment is 75 on the Shore D scale, and the durometers of the minor segments are 58, 40 and 25 on the Shore D scale, respectively.

14. The introducer sheath of claim 1, wherein each of said segments has a proximal end and a distal end, and wherein said segments are bonded at said ends to adjoining segments.

15. The introducer sheath of claim 1, wherein at least the distal end of the outer surface of said sheath is coated with a hydrophilic compound.

16. A sheath and catheter assembly, comprising:
a sheath having a proximal end and a distal end, said sheath comprising: an inner tube having a passageway extending longitudinally therethrough, said passageway having a substantially uniform diameter; a coil comprising a plurality of turns positioned longitudinally around said inner tube, said turns having a predetermined spacing therebetween; and an outer tube positioned longitudinally around said coil and connected to said inner tube through the spaces between said turns, said outer tube having a diameter of greater than 5 French, and said outer tube comprising a three distal tube segments, said segments aligned in order of decreasing durometer toward said distal end, wherein a third-most-distal tube segment is immediately proximal to a second-most-distal tube segment, which is immediately proximal from a most-distal tube segment, wherein the most-distal tube segment has a length of 3.2 cm and a durometer of between 20-30 on the Shore D scale, wherein the second-most-distal tube segment has a length of 5 cm and a durometer of between 35-45 on the Shore D scale, and wherein the third-most-distal tube segment has a length of 3 cm and a durometer of between 53-63 on the Shore D scale; and a catheter having an open proximal end, an open distal end, and a passageway extending longitudinally therethrough between said open proximal end and said open distal end, said catheter sized for insertion into said inner tube passageway, and further sized such that at least said distal end portion extends beyond the distal end of said sheath when said catheter is inserted into said inner tube passageway; said catheter distal end is dimensioned relative to said sheath distal end such that a generally smooth profile of said assembly is defined thereby, said catheter having a outer diameter that is 0.0005 to 0.004 inch (0.013 to 0.10 mm) less than said diameter of said inner tube passageway, the outer diameter of the catheter being less than a diameter of an opening at the distal end of the sheath.

17. The assembly of claim 16, wherein said outer diameter of the catheter is 0.001 to 0.003 inch (0.025 to 0.076 mm) less than said diameter of the inner tube passageway.

18. The assembly of claim 16, wherein at least the distal end of the outer surface of said sheath is coated with a hydrophilic compound.

19. The assembly of claim 16, wherein at least the distal end of the outer surface of the catheter is coated with a hydrophilic compound.

20. The assembly of claim 16, wherein the distal end of said catheter is shaped for access to a body vessel.

21. The assembly of claim 16, wherein said outer tube comprises a major segment of higher durometer comprising at least 75% of the length of the outer tube, arranged proximally from the three distal tube segments.

22. The assembly of claim 16, wherein said tapered distal end of said catheter has a curved configuration, said curved configuration corresponding to a vascular pattern at a target site within the anatomy of a patient for facilitating insertion of the catheter into said target site.

23. A flexible, kink-resistant introducer sheath having a proximal end and a distal end, comprising:
a lubricious inner tube having a passageway extending longitudinally therethrough, said passageway having a substantially uniform diameter of between 4 and 10 french;
a reinforcing member positioned longitudinally around said inner tube, said reinforcing member consisting essentially of a coil having a plurality of coil turns having a generally uniform spacing therebetween, wherein said coil turns extend between a proximal end and a distal end of said inner tube; and
an outer tube positioned longitudinally around the coil and the inner tube and connected to the inner tube through the spaces between said turns, said outer tube having a diameter of greater than 5 French, said outer tube comprising four tube segments aligned in order of decreasing durometer from said proximal end to said distal end of said introducer sheath, said tube segments comprising a major segment of higher durometer comprising more than 75% of the length of the outer tube, and three minor segments of lower durometer, and wherein the at least three minor segments are sized to access the common carotid, wherein a third-most-distal minor segment having a length of 3.0 cm is immediately proximal from a second-most-distal minor segment, wherein the second-most-distal minor segment having a length of 5 cm is immediately proximal from a most-distal segment, and wherein the most-distal minor segment has a length of 3.2 cm.

24. The introducer sheath of claim 23, wherein said inner tube comprises PTFE, said PTFE tube having a roughened outer surface, and wherein said outer tube is bonded to said inner tube at said roughened surface.

25. The introducer sheath of claim 23, wherein the durometer of said major segment is about 75 on the Shore D scale, and the durometers of the minor segments are about 58, 40 and 25 on the Shore D scale, respectively.

* * * * *